United States Patent
Wolf et al.

(10) Patent No.: US 10,900,928 B2
(45) Date of Patent: Jan. 26, 2021

(54) GAS SENSOR

(71) Applicant: Alcotek, Inc., Brentwood, MO (US)

(72) Inventors: Karl R. Wolf, Eureka, MO (US); Joe Fodor, Fenton, MO (US)

(73) Assignee: Alcotek, Inc., Brentwood, MO (US)

( * ) Notice: Subject to any disclaimer, the term of this patent is extended or adjusted under 35 U.S.C. 154(b) by 321 days.

(21) Appl. No.: 15/420,015

(22) Filed: Jan. 30, 2017

(65) Prior Publication Data

US 2017/0269025 A1    Sep. 21, 2017

Related U.S. Application Data

(60) Provisional application No. 62/288,219, filed on Jan. 28, 2016.

(51) Int. Cl.
| | | |
|---|---|---|
| *G01N 27/407* | (2006.01) | |
| *G01N 27/416* | (2006.01) | |
| *G01N 33/00* | (2006.01) | |
| *G01N 1/22* | (2006.01) | |

(52) U.S. Cl.
CPC .......... *G01N 27/4163* (2013.01); *G01N 1/22* (2013.01); *G01N 27/407* (2013.01); *G01N 33/0047* (2013.01)

(58) Field of Classification Search
None
See application file for complete search history.

(56) References Cited

U.S. PATENT DOCUMENTS

| | | | | |
|---|---|---|---|---|
| 4,770,026 A | * | 9/1988 | Wolf | G01N 33/4972 422/84 |
| 5,092,980 A | * | 3/1992 | Maurer | G01N 27/404 204/409 |
| 5,291,898 A | * | 3/1994 | Wolf | G01N 33/4972 422/84 |
| 8,702,935 B2 | | 4/2014 | Davis et al. | |
| 2007/0154765 A1 | * | 7/2007 | Bayer | G01N 33/4972 429/506 |
| 2010/0223975 A1 | * | 9/2010 | Lueck | G01N 33/4972 73/1.06 |
| 2013/0186776 A1 | * | 7/2013 | Scheffler | G01N 27/26 205/785.5 |

(Continued)

FOREIGN PATENT DOCUMENTS

EP    0 633 594 A1 *    7/1995    ............. G01N 33/00

OTHER PUBLICATIONS

Professional Brewers Analytical Services Catalog, Analytical Services, White Labs, Siebel Institute of Technology, San Diego, California, USA (12 pages).

(Continued)

*Primary Examiner* — J. Christopher Ball
(74) *Attorney, Agent, or Firm* — Lewis Rice LLC

(57) ABSTRACT

Fuel cell gas sensors using an aperture in a fuel cell gas sensor that allows for determination of a gas proportion in a sample that includes more gas than could otherwise be safely sampled. The aperture is adjustable between an open and a closed state. The amount of the gas of interest exposed to the fuel cell may be adjusted by adjusting the amount of time that the aperture is in the open state. Alternatively, the amount of the gas of interest exposed to the fuel cell may be adjusted by adjusting the size of the aperture.

12 Claims, 7 Drawing Sheets

(56) References Cited

U.S. PATENT DOCUMENTS

2013/0276553 A1* 10/2013 Yushko ................ E21B 49/086
73/863.86

OTHER PUBLICATIONS

Wang, Mei-Lang, et al., "A Rapid Method for Determination of Ethanol in Alocoholic Beverages Using Capillary Gas Chromatography," Journal of Food and Drug Analysis, vol. 11, No. 2, 2003, pp. 133-140 (8 pages).

Ueberfeld, Jorn, et al., "Determination of Henry's constant using a photoacoustic sensor," J. Chem. Thermodynamics, 2001, 33, pp. 755-764; doi:10.1006/jcht.2000.0776; http://www.idealibrary.com (10 pages).

"Determination of Ethanol Concentration in Aqueous Solutions," College of Science, University of Canterbury, http://www.outreach.canterbury.ac.nz/chemistry/documents/ethanol.pdf, printed on Dec. 15, 2014 (3 pages).

Liu, Nairui, et al., "A Simple Method for Measuring Methanol Content in Gas Field Wastewater," Bioinformatics and Biomedical Engineering, 2009, ICBBE 2009, 3rd International Conference held in Bejing, China on Jun. 11-13, 2009, 10.1109/ICBBE.2009.5162239 (Abstract) (1 page).

Beauchaine, Mike, "Measuring Water, Methanol and Total Glycerin in B100 Samples," Biodiesel Magazine, May 25, 2007, http://biodieselmagazine.com/articles/1663/measuring-water-methanol-and-total-glycerin-in-b100-samples/, printed on Dec. 15, 2014 (3 pages).

AOAC 984.14-1988, Ethanol in Beer, Gas chromatographic method, Journal of AOAC International vol. 67, 192, 1984 (1 page).

"An Introduction to Saturated Vapour Pressure," http://www.chemguide.co.uk/physical/phaseequi/vapourpress.html, printed on Jan. 7, 2015 (7 pages).

"Alcohol Fact Labeling Methods," Alcohol and Tobacco Tax and Trade Bureau, U.S. Department of Treasury, https://www.ttb.gov/ssd/labeling_methods.shtml, printed on Jul. 29, 2014 (2 pages).

Neame, Michael J. H., "Ethanol Measurement in Industrial Processing Using Fuel Cell Sensors," A Thesis submitted to the University of Wales Institute of Science and Technology, Department of Chemistry, Oct. 1981 (327 pages).

* cited by examiner

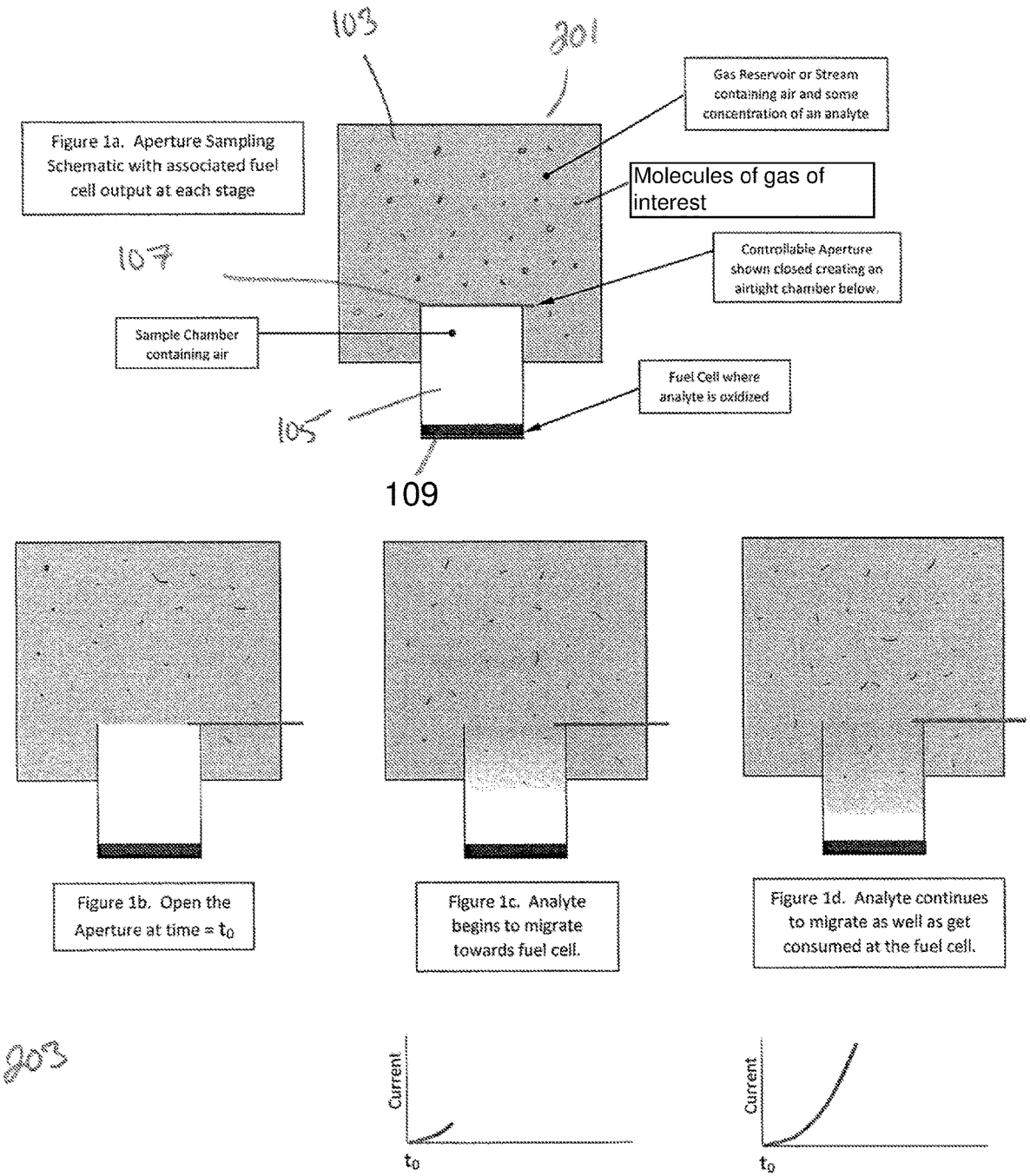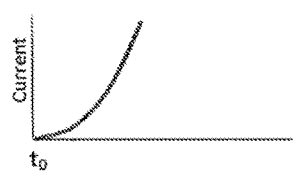

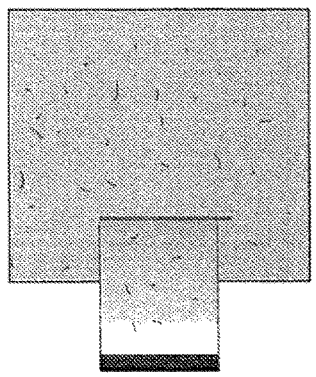
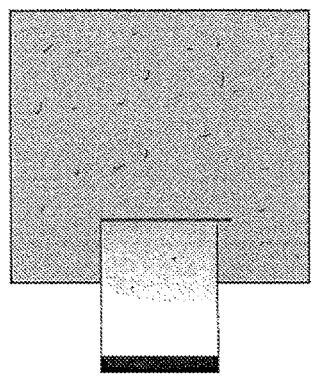
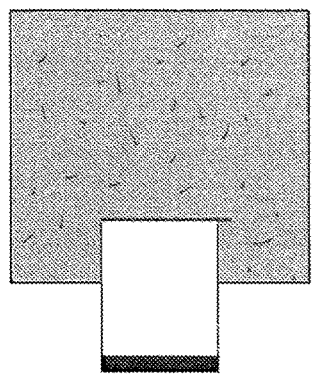
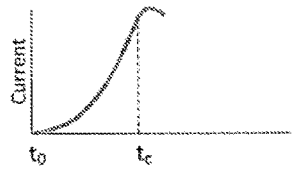
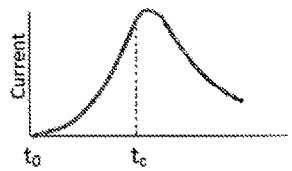
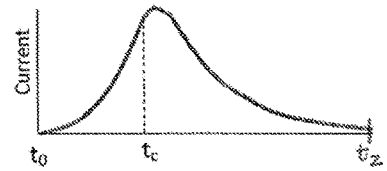
209
211
213

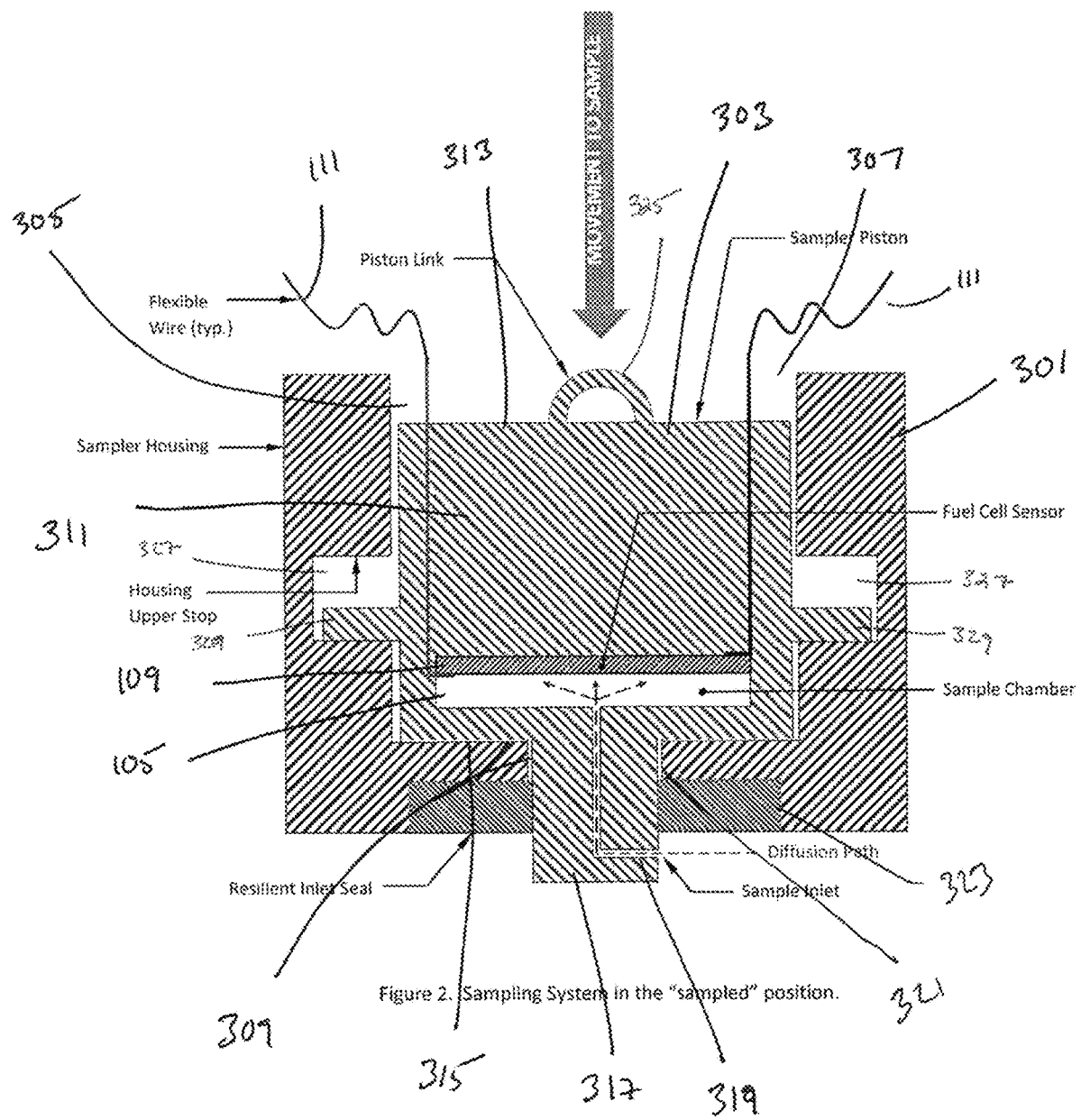

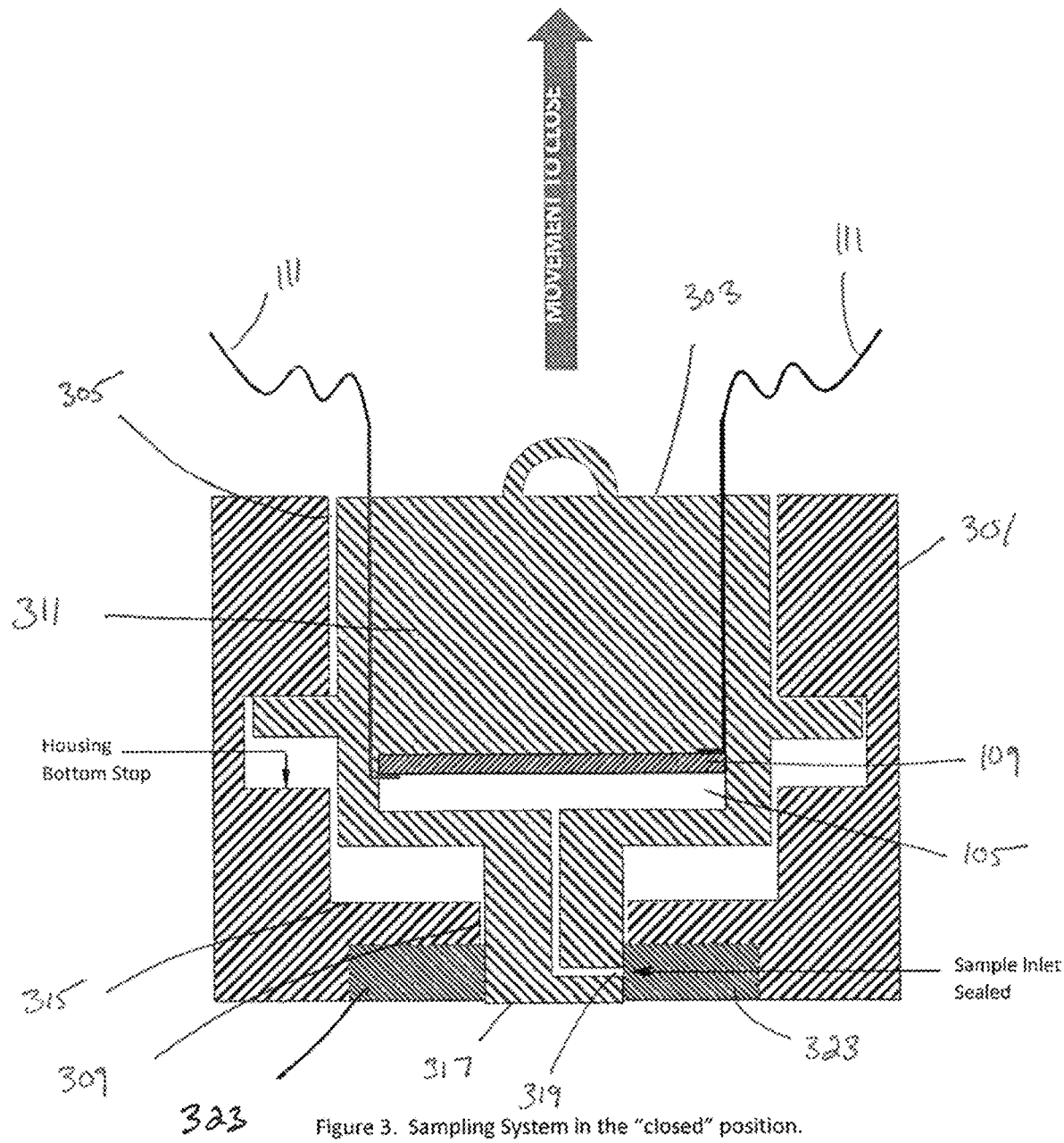
Figure 3. Sampling System in the "closed" position.

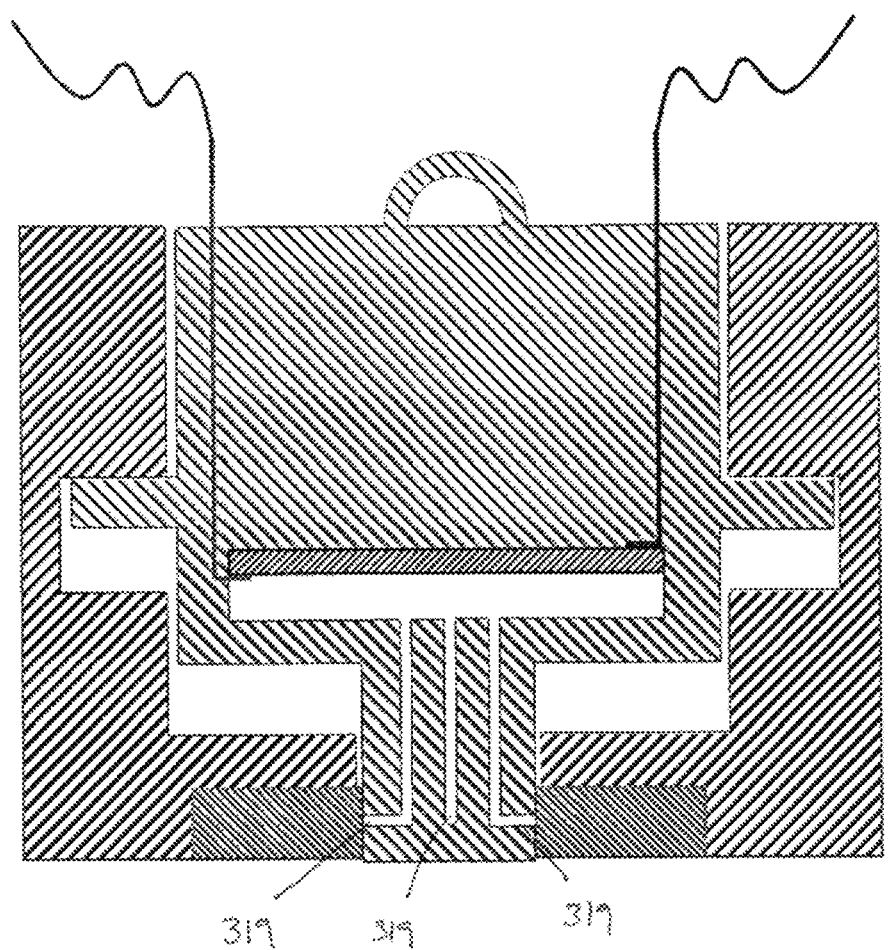
Figure 4. Showing Multiple Sample Inlets.

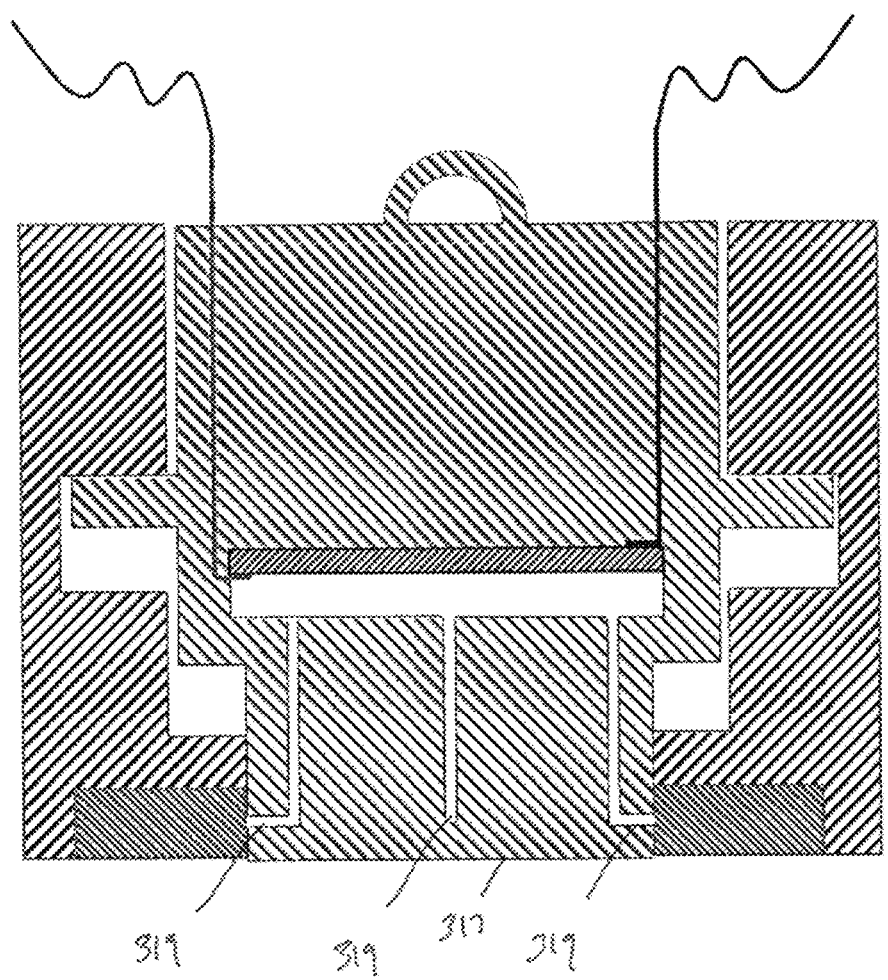
Figure 5. Showing Multiple Sample Inlets and Wider Piston.

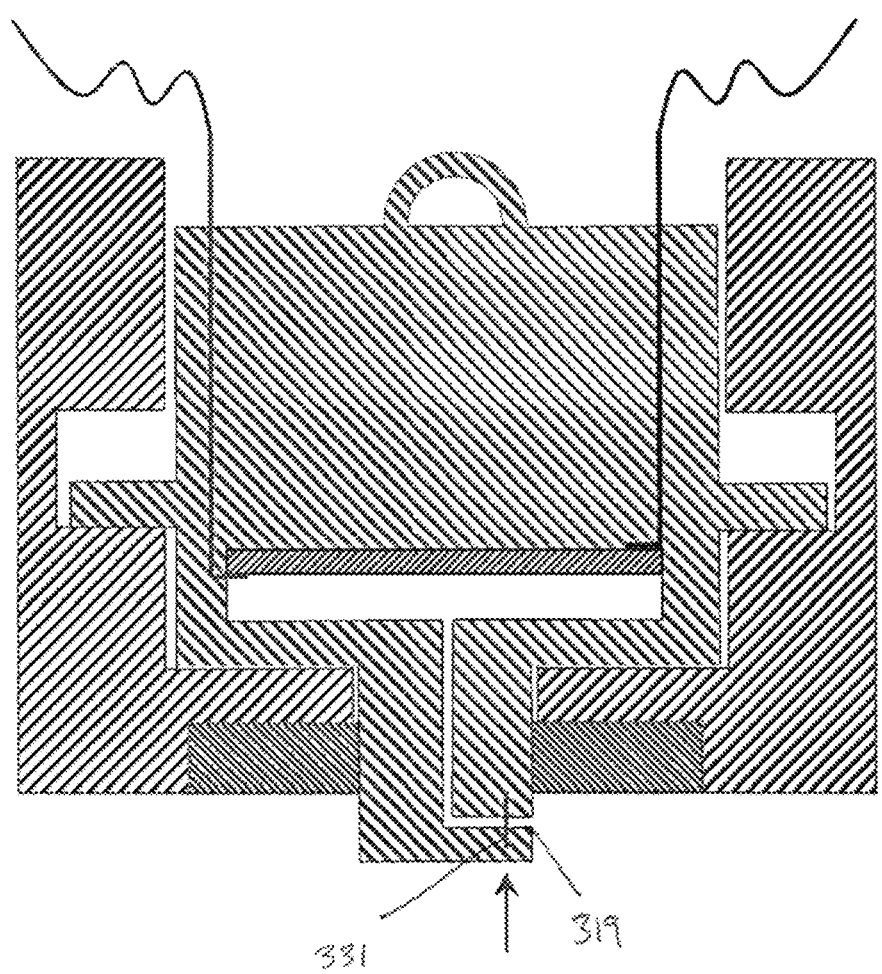
Figure 6. Adding a membrane in the diffusion path.

GAS SENSOR

CROSS REFERENCE TO RELATED APPLICATIONS

This application claims the benefit of U.S. Provisional Patent Application 62/288,219, filed Jan. 28, 2016, the entire disclosure of which is herein incorporated by reference.

BACKGROUND OF THE INVENTION

Field of the Invention

The present invention relates to gas sensors, and more particularly, to the use of an aperture in a fuel cell gas sensor that allows for determination of a has proportion in a sample that includes more gas than could otherwise be safely sampled.

Description of the Related Art

Gas sensors and systems employing gas sensors may be used to detect the presence of gases in a sample, or in the ambient atmosphere. Such sensors may detect the presence, amount, or concentration of a gas. Gas sensors are typically designed to detect particular types of gases while remaining unaffected by other gasses or as compounds not targeted for measurement. Gas sensors may be designed to detect any particular gas. For example gas sensors may be used to detect the presence of toxic, nauseous, combustible, flammable, or otherwise potentially dangerous or debilitating compounds. The reasons for needing such detection vary, but will often relate to human safety, such as radon and carbon monoxide detection. Alternatively, the reasons for detecting a particular gas may be to ensure the consistency of a gas, which may be an input gas to a process or an intermediary or final product of a process. In some cases, a gas detector may be used simply to determine that a certain event has occurred. For example, an alteration of the composition of a naturally vented gas from at or around a volcano may signal an impeding volcanic eruption. In some cases, a gas detector many be used simply to measure a quality of a gas of interest.

One way to implement gas detection is through use of a particular type of electrochemical cells, sometimes popularly known as "fuel cells." Typically, a fuel cell is a device that converts the chemical energy of a fuel into electricity through a chemical reaction. The outputted electricity is generally in the form of a current of electrons. In a typical fuel cell configured as a gas sensor, the chemical reaction is caused by the presence of the gas to be detected. In many applications, this chemical reaction is between positive hydrogen ions and oxygen or an oxidizing agent. This same basic principle applies to other electrochemical cells, such as batteries, except that batteries operate by reaction of two agents present in the battery and eventually lose their ability to provide electricity when those reactions are complete. By comparison, fuel cells can produce electricity continuously so long as the chemical inputs, or fuel and oxygen, are supplied. However, practically, fuel cells usually function until all the material in the fuel cell has been degraded, at which time the fuel cell needs to be replaced.

Fuel cells typically have a few components in common: an anode, a cathode, and an electrolyte that facilitates the movement of positive hydrogen ions (e.g., protons) between two opposing sides of the fuel cell. Typically, the electrolyte partitions the fuel into two different portions, one portion being an input for fuel and the other portion an input for oxygen. The anode and cathode generally comprise catalysts that cause the fuel and oxygen to undergo oxidation reactions that release both additional hydrogen ions and electrons. The hydrogen ions are drawn through the electrolyte during the reaction, while the electrons are drawn from the anode to the cathode through, an external circuit, producing electric current. The byproducts of this reaction often include water, formed at the cathode by the reaction of hydrogen ions with oxygen and electrons.

These fuel cells may be used to detect the presence of a given gas. The basic principle of operation is that the sensors react with the gas of interest and produce an electrical signal proportional to the concentration of the gas of interest in a sample in contact with the fuel cell. A "sensing electrode" (sometimes known in the art as a "working electrode") and a "counter electrode" are generally separated from one another by an electrolyte. When the gas of interest encounters the sensing electrode, typically it reacts and produces electrical current through a redox (oxidation or oxidation-reduction) reaction. Typically, these reactions are catalyzed by the electrode materials, which are specifically selected for the gas of interest. A gas-permeable membrane is generally disposed in many of these systems to keep the electrolyte within the cell while allowing vas to enter the sensor and contact the sensing electrode.

Fuel cells are implemented as gas sensors using a variety of techniques, generally distinguished by the means of sampling the gas source to be tested. For example, steady-state diffusion-based fuel cell gas sensors produce continuous current (or alternatively, continuous voltage) by supplying a continuous sample stream from a gas source to the gas sensor. The magnitude of the current depends on the concentration of the gas of interest. The rate of diffusion from the sample stream is typically controlled using various holes and/or membranes. Measurable electrical output is continuous while the gas of interest is present in the gas source but changes if the concentration of the gas of interest changes. Thus, the concentration of the gas of interest can be detected based on changes in the electrical output of the gas sensor over time. Additionally, membranes may be used to improve the selectivity of the gas sensor.

Another fuel cell gas sensor implementation is on-demand volume capture, in which the gas sensor is provided with a fixed volume sample of gas from a source at a specific time. The gas sensor produces a finite amount of current or voltage per sample depending on the concentration of the gas of interest in the sample. The sample is often collected from a gas flow to provide a representative sample of the concentration of the detected gas in the flow at the instant the sample is taken. Typically, in such gas sensors, the captured volume must be the same volume for all samples. Further, the measurable output of the gas sensor is finite and of short duration, as it only lasts as long as there is still oxidizable gas present in the sampled volume.

Steady-state diffusion-based gas sensors are generally more cost-effective than volume capture gas sensors, but they tend to provide more qualitative than quantitative measurements, and are known in the art to suffer from substantial calibration drift due to their continuous reaction. While diffusion-based gas sensors may be designed to measure higher concentrations by slowing the diffusion rate, such as through the use of lower-porosity membranes or smaller diffusion holes, these designs require an alternate mechanical design from the standard low-concentration sensor and are not amenable to real-time or on-demand changes in the gas sensor's measuring range. Even if such modifications were made, the resulting device would still be more qualitative than quantitative, and would still suffer from calibration drift problems.

Volume capture gas sensors tend to be more expensive, but provide higher degrees of measurement accuracy and superior calibration stability than steady-state diffusion gas sensors. However, volume capture gas sensors are typically only used for measuring low gas concentrations. This is due to the fact that the typical fuel cell electrodes in a volume capture gas sensor would have to be substantially increased in size to avoid overwhelming the device in samples with high gas concentrations. Since many such devices use platinum or other precious metal electrodes, manufacturing a fuel cell with larger electrodes can be prohibitively expensive. Further, increasing the electrode size while keeping the volume of the sample capture very low presents difficult engineering challenges.

The invention provides an enhanced volume capture gas sensor that is capable of measuring samples of varying concentrations of a gas of interest.

SUMMARY OF THE INVENTION

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Described herein, amongst other things, is a gas sensor comprising a sample chamber adjacent to a gas reservoir, the gas reservoir including a sample having a proportion of a gas of interest; a fuel cell within the sample chamber, the fuel cell configured to produce an electric current proportional to an amount of the gas of interest in contact with the fuel cell; and an aperture disposed between the sample chamber and the gas reservoir; wherein the aperture is adjusted between an exposed state, which exposes the sample chamber to the gas reservoir, and a covered state, which seals the sample chamber fro tam the gas source; and wherein the aperture is only in the exposed state for a period of time which is insufficient for a proportion of the gas of interest within the sample chamber to reach the proportion of the gas of interest in the gas reservoir.

In an embodiment of the gas sensor, the aperture comprises a sampler piston and movement of the sampler piston adjusts the aperture between the exposed state and the closed state.

In an embodiment of the gas sensor, the gas sensor further comprises a recess formed within a housing for the sampler piston and a flange formed on an exterior of the sampler piston, wherein the flange is disposed in the recess so that movement of the sampler piston is restricted.

In an embodiment of the gas sensor, the aperture includes a membrane configured to prohibit flow of a liquid into the sample chamber.

In an embodiment of the gas sensor, the aperture includes a membrane configured to restrict diffusion of the gas of interest into the sample chamber.

In an embodiment of the gas sensor, the gas of interest is ethanol.

There is also described herein, in an embodiment, a method for determining a proportion of a gas of interest from a gas source, the method comprising providing a gas sensor comprising a sample chamber; a fuel cell within the sample chamber, the fuel cell configured to produce an electric current proportional to an amount of a gas of interest in contact with the fuel cell; and an aperture moveable between an exposed state and a closed state; positioning the gas sensor adjacent to a gas source, the gas source including a proportion of a gas of interest; adjusting the aperture between the exposed state, which exposes the sample chamber to the gas source, and a closed state, which seals the sample chamber from the gas source; wherein the aperture is only in the exposed state for a period of time which is insufficient for a proportion of the gas of interest within the sample chamber to reach the proportion of the gas of interest in the gas source; and generating a closed curve of electric current from the fuel cell, an area under the closed curve being indicative of the proportion of the gas of interest in the gas source.

In an embodiment of the method, in the positioning, the gas sensor is positioned adjacent to a known gas source, the proportion of the gas of interest within the known gas source being known and constant.

In an embodiment of the method, in the generating, the area under the closed curve comprises a calibration area indicative of the known concentration of the gas of interest in the known gas source; and storing the calibration area.

In an embodiment of the method, the method further comprises repeating the method on an unknown gas source; and comparing the area under the curve for the unknown gas source to the calibration area.

In an embodiment of the method, a size of the aperture is adjusted based on an anticipated concentration of the gas of interest.

In an embodiment of the method, the size of the aperture is adjusted by incompletely opening the aperture.

In an embodiment of the method, a size of the aperture is adjusted based on the closed curve.

In an embodiment of the method, the size of the aperture is adjusted by incompletely opening the aperture.

In an embodiment of the method, the gas of interest is ethanol.

In an embodiment of the method, the proportion of the gas of interest is determined from a portion of the total area under the closed curve.

In an embodiment of the method, the proportion of the gas of interest is determined from a whole of the total area under the closed curve.

In another embodiment of the gas sensor, the gas sensor comprises a sample chamber adjacent to a gas reservoir, the gas reservoir including a proportion of a gas of interest; a fuel cell within the sample chamber, the fuel cell configured to produce an electric current proportional to an amount of the gas of interest in contact with the fuel cell; an aperture disposed between the sample chamber and the gas reservoir; and a means for adjusting the aperture between an exposed state, which exposes the sample chamber to the gas reservoir, and a covered state, which seals the sample chamber from the gas source, wherein the means for adjusting adjusts the aperture to the exposed state only for a period of time which is insufficient for a proportion of the gas of interest within the sample chamber to reach the proportion of the gas of interest in the gas reservoir.

BRIEF DESCRIPTION OF THE DRAWINGS

FIGS. 1a, 1b, 1c, 1d, 1e, 1f, and 1g depict, in order, an embodiment of an aperture sampling method utilizing a sampling system depicted in generic block diagram.

FIG. 2 depicts a cross-sectional diagram of an embodiment of a sampling device in a sampling position that can carry out an embodiment of an aperture sampling method. The device is depicted in the sampling position.

FIG. 3 depicts the embodiment of FIG. 2 in a closed or non-sampling position.

FIG. 4 depicts an alternative embodiment of a sampling device in the closed position.

FIG. 5 depicts another alternative embodiment of a sampling device in the closed position.

FIG. 6 depicts the embodiment of FIG. 2 with the addition of a membrane to inhibit liquid flow into the sample chamber or to control gaseous diffusion.

DETAILED DESCRIPTION OF PREFERRED EMBODIMENT(S)

The following detailed description and disclosure illustrate by way of example and not by way of limitation. This description will clearly enable one skilled in the art make and use the disclosed structures and methods, and describes several embodiments, adaptations, variations, alternatives and of the disclosed structures and methods. As various changes could be made in the above constructions without departing from the scope of the disclosures, it is intended that all matter contained in the description or shown in the accompanying drawings shall be interpreted as illustrative and not in a limiting sense.

FIGS. 1a through 1g depict an exemplary embodiment of an aperture sampling method and associated gas sensor cording to the present disclosure. In the depicted embodiment of FIGS. 1a-1g, the method is implemented via a fuel cell device having a fuel cell (109) disposed within sampling chamber (105). The depicted sampling chamber (105) is connected to, and separated from, a gas reservoir (103) by an aperture (107). When the aperture (107) is an open, or exposed, state, the sampling chamber (105) is in fluid communication with the gas reservoir (103). In the depicted embodiment, the depicted fuel cell (109) is configured to break down ethanol and create electrical current in the process and would be suitable for use as a breath alcohol detector or other device useful for detecting presence and quantity of ethanol. Gas reservoir (103) is intended to be representative of a small or large volume closed or open, static of flowing, and is presented in general block form in the FIGS. 1a through 1g for simplicity of illustration. Fuel cell (109) may be configured to breakdown and detect any suitable gas of interest. Some fuel cells may be capable of detecting multiple gasses, or alternatively, only a single gas. In the present disclosure, gas shall mean a gas, a gas compound, a vapor, a suspension of molecules in a gas, or any similar composition.

The device state prior to the start of the method is described with reference to FIG. 1a. The aperture (107) is in a closed state, where the aperture (107) is not exposed to the gas reservoir (103), and there is a gas or a gas mixture in the sampling chamber (105) that will not react with the fuel cell (109). In an embodiment, the gas in the sampling chamber is essentially atmospheric ambient air (or other gas with no sample of interest), mostly comprising nitrogen, oxygen, hydrogen and water vapor, with other constituent gases as well. In the depicted embodiment, there will be little or no ethanol in the chamber (105) because any ethanol present in the chamber (105) will have been consumed by the fuel cell (109) previously, had any been present. The aperture (107) in its closed state has a sufficiently tight seal between the sampling chamber (105) and the gas reservoir (103). Typically, this seal will be an airtight seal. In some exemplary embodiments, the aperture (107) may include as sealing member that assists in creating a seal for the aperture (107). The gas reservoir (103) generally also contains the same mixture of ambient air as does the sampling chamber (105). The volume of as in the sampling chamber (105) is generally the same whether the aperture (107) is in an open or a closed state, meaning the pressure and temperature are about the same inside the chamber (105) as outside with only minor variations that may naturally result from, for example, insulating properties of the sampling chamber (105) or heat transmission or absorption from the sampling chamber (105) walls. Typically, at some point in time before the start of the method, gas chamber (103) is exposed to, and subsequently consists of, the gas flow or volume to be detected and analyzed. Alternatively, the gas chamber (103) is exposed to the gas flow after the start of the method.

A note is merited concerning the relationship between qualitative descriptions of certain properties and the quantative ranges described by them. One of ordinary skill in the art will understand that them almost always exists, at a sufficient level of precision, a qualitative difference between any two measures of a given property (e.g., temperature, pressure, volume, mass, concentration, time, etc.). For purposes of this disclosure, one of ordinary skill in the art will understand that qualitative descriptions of these and other physical and chemical properties, whether or not prefaced by terms such as "generally" and "about," describe a range of quantities effective for the system to operate as described in the context of this disclosure and the physical and chemical properties and reactions on which it relies.

By way of example and not limitation, one of ordinary skill in the art will understand that when a volume of gas is sealed in an enclosed chamber but no other forces are applied to it, that sealed volume of gas will generally maintain the same temperature, pressure, and concentration characteristics of the ambient air from which it was sampled, though minor variations may naturally occur, such as through interactions with the chamber walls and natural particle distribution in the sample and chamber. Regardless, one of ordinary skill in the art will understand that the temperature, pressure, and concentration of the inside and outside gases are effectively "the same" for purposes of this disclosure. However, it should be noted that the fuel cell technology described herein may use wet chemistry. In these cases, water vapor concentrations may vary more substantially and still fall within the effective ranges described herein.

In the next step (203), as shown in FIG. 1b, the aperture (107) is adjusted to an open state allowing the gas previously introduced to the sampling chamber (105) to interact with gas in the reservoir (103). For purposes of this disclosure, the time of opening of the aperture (107) is referred to as $t_0$. To the extent that gases are not in equilibrium between the sampling chamber (105) and gas reservoir (103), diffusion of the gasses will begin from the direction of higher concentration to lower. Because the concentration, temperature, and pressure of the main constituent gases in the sampling chamber (105) (e.g., nitrogen, oxygen) are the same on both sides of the aperture (107), little to no diffusion takes place with respect to these constituents. In the depicted embodiment, the gas not present in the sampling chamber (105) in FIG. 1a is ethanol.

Next, as depicted in FIG. 1c, if any ethanol is present in the ambient air of the gas reservoir (103), the ethanol will immediately begin to diffuse (205) from higher concentration in the gas reservoir (103) to lower concentration (e.g., little to no concentration) in the sampling chamber (105), in order to reach equilibrium. Next, as depicted in FIG. 1d, when the diffusing ethanol reaches the fuel cell (109), the ethanol begins to break down (207) according to known chemical principles, creating electrical current in the process.

Soon after the ethanol begins to diffuse (205) into the sampling chamber (105), the ethanol's mass and concentration in the sampling chamber (105) increase. However, as time passes and the ethanol reaches the fuel cell (109), the ethanol breaks down as it interacts with the fuel cell (109). As the fuel cell (109) consumes ethanol, the ethanol's mass in the sampling chamber (105) becomes a function of the diffusion rate of the ethanol into the sampling chamber (109) and the consumption rate of the fuel within the fuel cell (109). The electrical current produced by fuel cell (109) increases (207) as the concentration of ethanol in the sampling chamber (109) increases. So long as the aperture (107) remains in the open state, this cycle of diffusion into the sampling chamber (109) and breakdown at the fuel cell (109) continues. Rather than allow this process to continue in a steady state manner ad infinitum, the aperture (107) is adjusted to the closed state (209) after a pre-determined period of time, as seen in FIG. 1e. Adjusting (209) the aperture (107) to the closed state re-forms the seal between the sampling chamber (105) and gas reservoir (103), allowing no further ethanol to enter the sampling chamber (105). The time at which the aperture (107) enters the closed state is referred to as $t_c$. Alternatively, the aperture closed state reduces diffusion of the gas of interest to an acceptable level. A person having ordinary skill in the art would understand that the aperture (107) may be adjusted between its closed and open states using any known device, means, or method.

Next, the remaining ethanol in the sampling chamber (105) continues to react (211) with an electrode of the fuel cell (109) to produce electricity, breaking down until there is no more ethanol (213) in the sampling chamber (105). From this point on (209), the amount of current produced by the fuel cell (109) in the sampling chamber (105) will fall until the ethanol has been consumed and the current reaches zero (213). In the depicted embodiment, the point in time at which the current returns to zero is referred to as $t_z$. By adjusting the aperture (107) to the closed state before any equilibrium can occur between ethanol diffusion and breakdown, a closed curve with a single peak (no plateau) is created. In the depicted embodiment, such a curve shape indicates the fuel cell (109) is not overwhelmed by too much ethanol being supplied and thus the measurement techniques outlined below will be effective. In the event the curve plateaued, the fuel cell (109) would have received a higher ethanol concentration than it can effectively process. In one embodiment, the aperture sampling would provide a 0.010" diameter aperture size, a $t_c$ of 0.5 seconds, and an initial $t_z$ of 30 seconds. In other embodiments, the aperture size, $t_c$, and $t_z$ may vary.

The total amount of energy produced by the fuel cell (109) in this process may then be computed or measured. This may be done, for example, by integrating the current carve from $t_0$ to $t_c$, from $t_0$ to $t_z$, or another range of measurements over time, or otherwise approximating the area under the curve using known techniques or software. The area under any portion of the current curve may be computed or measured. In a typical fuel cell, $t_z$ can and will increase over the life of the fuel cell, but without affecting the integral for a given concentration of the gas of interest.

The laws of diffusion provide that higher concentrations of the gas of interest (in this depicted embodiment, ethanol) outside of the sampling chamber (105) diffuse into the chamber (105) at a proportionally faster rate, than would lower concentrations of that gas. If the time that the aperture (107) remains in the open position is held constant from calibration to use, more total molecules of ethanol will diffuse into the sampling chamber (105) from a higher concentration outside the sampling chamber (105) (e.g., in the gas reservoir (103)) than would diffuse into the sampling chamber (105) from a lower concentration outside of the sampling chamber (105). Because the amount of current generated by the depicted fuel cell (109) is dependent on the amount of the gas of interest in the chamber, a proportionally higher amount of electricity will be produced by the fuel cell (109) from the higher concentration than the lower of the gas of interest in the gas reservoir (103).

Different scales of measurement of the gas of interest for the fuel cell (109) can easily be created. By way of example and not limitation, the amount of time that the aperture (107) is in the open state may be varied to set a different calibration standard. That is, for a higher concentration of gas, a shorter amount of time that the aperture (107) is in the open state may be used because the rate of diffusion will be much higher. A shorter aperture open time may be important to prevent damage to the fuel cell (109), as a large concentration could overwhelm a small fuel cell (109) and produce meaningless measurements. By reducing the aperture open time, the total exposure of the gas of interest to the fuel cell (109) is limited. By contrast, if lower concentrations are anticipated, a longer aperture open time may be appropriate and can be used both for calibration and measurement. Thus, the same gas sensor may be used for highly accurate readings in high gas concentrations by setting a short aperture open time and allowing little diffusion of a large quantity of the material of interest and in a low gas concentration by having a longer aperture open time and allowing large diffusion of a small quantity of the gas of interest. As noted previously, these two modes of operation will generally not be used interchangeably, but the gas sensor will be calibrated for one or the other by utilizing a calibration gas of generally expected and known concentration, and calibrating using a set aperture open time. It may be that a single calibration will suffice for all measurement ranges taking into account how calibration values change proportionally to changes in $t_c$.

Alternatively, the aperture size may be varied to control the diffusion rate of the gas of interest. By way of example and not limitation, the size of the aperture (107) may be varied to set a different calibration standard. That is, for a higher concentration of gas, a smaller size for aperture (107) may be used because the rate of diffusion will be much higher. A smaller size of aperture (107) may prevent damage to the fuel cell (109), as a large concentration could overwhelm a small fuel cell (109) and produce meaningless measurements. By reducing the aperture size, the total exposure of the gas of interest to the fuel cell (109) is limited. By contrast, if lower concentrations are anticipated, a larger aperture size may be appropriate and can be used both for calibration and measurement. The aperture size may be controlled by, for example, controlling the extent to which the aperture (107) is exposed to the gas reservoir (103). Accordingly, both the aperture open time and aperture size may be used to control the amount of the gas of interest that interacts with the fuel cell (109).

FIGS. 2-3 depict a cross-section diagram of an embodiment of a device implementing an embodiment of the method discussed above. The depicted device, generally a gas sensor, typically comprises a housing (301) having a recess (305) therein sized and shaped to surround a sampler piston (303), which travels through the recess (305) in a generally reciprocating motion. The depicted recess (305)

has two opposing ends an open top end (307) and an opposing bottom end (309). The depicted sampler piston (303) comprises a generally cylindrical main body (311) sized and shaped to fit into the recess (305). In the depicted embodiment, the sampler piston (303) main body (311) has a circular cross-section. In other embodiments, the sampler piston (303) main body (311) has cross-sectional shape that is a square, a rectangle, or any other shape.

The depicted sampler piston (303) main body (311) has a top end (313) and an opposing bottom end (315), with a second, smaller cylindrical member (317) rigidly attached to the bottom end (315) and generally coaxial with the main body (311). Like the main body (311), the cylindrical member (317) can have a circular cross-section, or any other shaped cross-section. The housing (301) also comprises a hole disposed at the bottom of the recess (305), the hole being sized and shaped to accommodate cylindrical member (317). The hole is generally through the housing (301). When assembled, main body (311) is disposed in the recess (305), and cylindrical member (317) is disposed in the hole (321).

The main body (311) contains a sampling chamber (105) in fluid communication with a fuel cell sensor (109), which in turn is in electrical communication with a pair of wires (111) to connect the fuel cell (109) to an external circuit. The second, smaller cylindrical member (317) comprises a gas sample inlet (319) in fluid communication with the sampling chamber (105). The depicted inlet (319) is also in fluid communication with the ambient environment only when the piston (303) is in the "open" or sampling position (or state) as depicted in FIG. 2. In the depicted embodiment, the cylindrical member (317) is sized and shaped so that when the piston (303) is disposed in sampling position, a portion of the cylindrical member (317) extends beyond the outer wall of the housing (301). In the depicted embodiment, the sampler piston (303) moves. The movement is typically linear. In other embodiments, the housing (301) may move while the sampler piston (303) also moves, or is stationary. In yet other embodiments, the movement of either the piston (303) or housing (301) is non-linear. Non-linear movement, by way of example and not limitation, may be rotational, or any other suitable movement.

The inlet (319) is disposed on the cylindrical member (317) such that when the piston (303) is disposed in sampling position, the inlet (319) is on the portion of the cylindrical member (317) extending beyond the outer wall of the housing (301), and thus the inlet (319) is in fluid communication with the ambient environment, and in turn places the ambient environment in fluid communication with the sample chamber (105). In the depicted embodiment, the inlet (319) includes a linear channel extending perpendicularly from the sample chamber to a right angle and then exiting the smaller cylindrical member (317) at a point on the side far enough towards the distal end of the member (317) to be in fluid communication with the ambient environment when the piston (303) is in sampling position (for example, at maximum depth into the recess (305)). In other embodiments, the inlet (319) may take any shape, size, or path. Further, in other embodiments, the channels associated with inlet (319) may take any shape, size, or path.

FIG. 3 depicts the same device as depicted in FIG. 2, but in "closed" or non-sampling position (or state). In the depicted embodiment of FIG. 3, the sampler piston (303) is partially withdrawn from the recess (305), causing the second cylinder member (317) to withdraw into the hole (321). The inlet (319) is disposed on the cylinder member (317) such that when the piston (303) is withdrawn into the housing (301), a sufficient portion of the cylinder member (317) is withdrawn into the hole (321) that the inlet (319) is disposed within the outer wall of the housing (301). In the depicted embodiment, a sealing element (323) is disposed at the portion of the hole (321) nearest the outer wall of the housing (301) such that when the cylinder member (317) is withdrawn into the hole (321), the inlet (319) is further covered by the sealing element (323), forming an airtight seal to inhibit or prevent ambient from entering the sampling chamber (105). In the depicted embodiment, the sealing element (323) is a sealing means. In a still further embodiment, the sealing element or sealing means is an O-ring, a rubber washer, or overmolded thermoplastic. In other embodiments, some other port on of the gas sensor may move to obstruct the inlet (319).

The depicted sampler piston (303) is loosely constrained by the housing (301). An airtight seal is not necessary as between the main body (311) and main recess (305). However, the fit between the cylindrical member (317) and the sealing element (323) is generally tighter to maintain an airtight seal over the inlet (319) when the device is in closed position.

The device is generally used by placing the bottom end of the housing (301) toward the sampling direction (e.g., the ambient air, or a pipe, channel, or stream containing the gas of interest) while closed. The reciprocating sampler piston (303) is then moved to the open position, exposing the inlet (319) to the environment to be sampled, and allowing diffusion to cause the gas of interest to migrate into the sampling chamber (105) via the inlet (319) and undergo redox reactions with the fuel cell (109). After the predetermined sampling time window passes, or aperture open time, the sampler piston (303) is withdrawn, re-establishing the seal over the inlet (319), and any remaining gas of interest in the inlet (319) and/or sampling chamber (105) reacts with the fuel cell (109) until concentration drops to zero in the inlet (319) and/or sampling chamber (105). FIGS. 4 and 5 depict alternative embodiments with varying geometries and multiple inlets (317).

In order to inhibit liquid from entering the sampling chamber (105), any or all of the inlets (319) may include a gas permeable membrane (331) to generally restrict liquid flow into the sampling chamber (105) while allowing gas to freely flow. Such a membrane (331) may also be used to control the rate of gas diffusion instead of relying on the size of the sample inlet (319). For example, in an embodiment where it is impractical to fabricate an inlet as small as would be required for a desired rate of gas diffusion from the sample to be tested, a membrane (331) may be used to reduce gas diffusion. Certain membranes (331) can also be used to make the gas sensor more specific to certain gas detection by restricting the diffusion of certain gases versus others, FIG. 6 provides an embodiment of how the membrane (331) can be positioned in the embodiment of FIG. 2. Further, the number of exposed inlets (319) may be used to control the diffusion rate, where the gas sensor is configured to move to several positions, at least some of the different positions exposing a different number of inlets (319).

In an embodiment, the device includes structures to constrain the reciprocating action. By way of example and not limitation, in the depicted device of FIG. 2, the main recess (305) into which the main body (311) of the sampler piston (303) is disposed further comprises an interior, cylindrical relief (327) having a diameter larger than that of the recess (305). In other embodiments, cylindrical relief (327) may have a cross-section that is a square, a rectangle, or any other shape. The relief (327) is sized and shaped to accept a protruding flange (329) on the main body (311). The relief (327) and flange (329) cooperate to limit the range of motion of the sampler piston (303), preventing it from retracting too far and thus causing the inlet (317) to slip past the sealing element (323) and thereby be exposed to ambient air. The relief (327) can also prevent the sampler piston (303) from being disposed too far, though the bottom of the main body (311) will impact the bottom of the main recess (305) and can also serve the same function.

The wires (111) are generally connected to an electrical circuit that includes, or is connected to, componentry for reading the amount of the current. The external circuit generally comprises a gas meter or gas reader, and may include other components appropriate for such a reader, such as user-operable controls for configuring and activating the reader, and outputs such as a display, sounds, or lights. The wires may also terminate in a device connectable to a mobile computing device, which then provides the user input/output functions. The depicted sampler piston (303) is typically operated by a mechanical or electromechanical device that drives the sampler piston forward and back. Such devices are known in the art, and may be connected to the sampler piston (303) via a piston link (325) rigidly attached to the top of the sampler piston (303). Such devices may alternatively be connected to the housing (301).

While the supplied drawings and discussed embodiments depict a geometry for sampling systems that may implement embodiments of the methods described herein, other geometries are also possible as would be understood by one of ordinary skill in the art.

While the invention has been disclosed in connection with certain disclosed embodiments, this should not be taken as limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method for determining a proportion of a gas of interest from a gas source, the method comprising:
   providing a gas sensor comprising:
      a sample chamber;
      a fuel cell within said sample chamber, said fuel cell configured to produce an electric current proportional to an amount of a gas of interest in contact with said fuel cell; and
      an aperture moveable between an exposed state and a closed state;
   positioning said gas sensor adjacent to a gas source, said gas source including a proportion of a gas of interest;
   adjusting said aperture between said exposed state, which exposes said sample chamber to said gas source, and a closed state, which seals said sample chamber from said gas source; wherein said aperture is only in said exposed state for a period of time which is insufficient for a proportion of said gas of interest within said sample chamber to reach said proportion of said gas of interest in said gas source; and
   generating a closed curve of electric current from said fuel cell, an area under said closed curve being indicative of said proportion of said gas of interest in said gas source.

2. The method of claim 1, wherein, in said positioning, said gas sensor is positioned adjacent to a known gas source, said proportion of said gas of interest within said known gas source being known and constant.

3. The method of claim 2, wherein, in said generating, said area under said closed curve comprises a calibration area indicative of said known concentration of said gas of interest in said known gas source; and storing said calibration area.

4. The method of claim 3, further comprising repeating said method of claim 1 on an unknown gas source; and comparing said area under said curve for said unknown gas source to said calibration area.

5. The method of claim 1, wherein a size of said aperture is adjusted based on an anticipated concentration of the gas of interest.

6. The method of claim 5, wherein said size of said aperture is adjusted by incompletely opening said aperture.

7. The method of claim 1, wherein a size of said aperture is adjusted based on said closed curve.

8. The method of claim 7, wherein said size of said aperture is adjusted by incompletely opening said aperture.

9. The method of claim 1, wherein said gas of interest is ethanol.

10. The method of claim 1, wherein said proportion of said gas of interest is determined from a portion of the total area under said closed curve.

11. The method of claim 1, wherein said proportion of said gas of interest is determined from a whole of the total area under said closed curve.

12. A gas sensor comprising:
   a sample chamber adjacent to a gas reservoir, said gas reservoir including a sample having a proportion of a gas of interest;
   a fuel cell within said sample chamber, said fuel cell configured to produce an electric current proportional to an amount of said gas of interest in contact with said fuel cell; and
   an aperture disposed between said sample chamber and said gas reservoir; wherein said aperture is adjusted between an exposed state, which exposes said sample chamber to said gas reservoir, and a covered state, which seals said sample chamber from said gas reservoir;
   wherein said aperture is only in said exposed state for a period of time which is insufficient for a proportion of said gas of interest within said sample chamber to reach said proportion of said gas of interest in said gas reservoir;
   wherein said fuel cell consumes said gas of interest within said sample chamber producing a closed curve of electric current, an area under said closed curve being indicative of said proportion of said as of interest in said gas reservoir,
   wherein said gas sensor comprises a sampler piston and movement of said sampler piston adjusts said aperture between said exposed state and said closed state; and
   wherein said sample chamber is disposed in said sampler piston.

* * * * *